(12) United States Patent
Mitsui

(10) Patent No.: US 9,285,577 B2
(45) Date of Patent: Mar. 15, 2016

(54) MICROSCOPE SYSTEM AND DATA DISTRIBUTION SYSTEM

(75) Inventor: Masanori Mitsui, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 932 days.

(21) Appl. No.: 13/214,537

(22) Filed: Aug. 22, 2011

(65) Prior Publication Data
US 2012/0081534 A1    Apr. 5, 2012

(30) Foreign Application Priority Data

Sep. 30, 2010   (JP) .................................. 2010-222804

(51) Int. Cl.
| | |
|---|---|
| G02B 21/36 | (2006.01) |
| G01N 21/25 | (2006.01) |
| G06T 7/40 | (2006.01) |
| G01J 3/46 | (2006.01) |

(52) U.S. Cl.
CPC ................. *G02B 21/365* (2013.01); *G01J 3/46* (2013.01); *G01N 21/25* (2013.01); *G06T 7/408* (2013.01)

(58) Field of Classification Search
None
See application file for complete search history.

(56) References Cited

U.S. PATENT DOCUMENTS

| | | | | |
|---|---|---|---|---|
| 5,732,150 A | * | 3/1998 | Zhou et al. ..................... | 382/133 |
| 7,133,547 B2 | * | 11/2006 | Marcelpoil et al. ........... | 382/129 |
| 7,171,030 B2 | * | 1/2007 | Foran et al. .................... | 382/128 |
| 2005/0071087 A1 | | 3/2005 | Anderson | |
| 2008/0218779 A1 | * | 9/2008 | Shirasawa ....................... | 358/1.9 |
| 2010/0201800 A1 | * | 8/2010 | Yamamoto et al. ............. | 348/79 |

FOREIGN PATENT DOCUMENTS

| | | |
|---|---|---|
| JP | 07-120324 | 5/1995 |
| JP | 2001-27624 A | 1/2001 |
| JP | 2005-233803 A | 9/2005 |
| JP | 2007-507770 A | 3/2007 |
| JP | 2008-232654 A | 10/2008 |
| JP | 2009-245674 | 10/2009 |
| JP | 2010-134195 A | 6/2010 |
| JP | 2010-169596 A | 8/2010 |

OTHER PUBLICATIONS

Yang, Lin, O. Tuzel, W. Chen, P. Meer, G. Salaru, L. Goodell, and D. Foran, "PathMiner: A Web-Based Tool for Computer-Assisted Diagnostics in Pathology", IEEE Transactions on Information Technology in Biomedicine, vol. 13, No. 3, May 2009.*
Japanese Office Action dated Jan. 28, 2014 from related Japanese Application No. 2010-222804, together with an English language translation.
Japanese Official Action dated Jul. 8, 2014 received from related Japanese Patent Application No. JP 2010-222804.

* cited by examiner

*Primary Examiner* — William C Vaughn, Jr.
*Assistant Examiner* — Lindsay Uhl
(74) *Attorney, Agent, or Firm* — Scully, Scott, Murphy & Presser, P.C.

(57) ABSTRACT

A microscope system includes a microscope apparatus, a pigment content converter, a property information adding unit, and a communication unit. The microscope apparatus acquires, by using a microscope, a pathology specimen image of a pathology specimen stained with a predetermined pigment. The pigment content converter converts, by using pigment spectral data, pixel values of the pathology specimen image to the pigment content at corresponding sample points on the pathology specimen. The property information adding unit generates conversion image data by adding the pigment spectral data, which is used for the conversion, to the pigment content of each pixel that is converted by the pigment content converter. The communication unit transmits the conversion image data to a terminal device.

11 Claims, 11 Drawing Sheets

MICROSCOPE SYSTEM AND DATA DISTRIBUTION SYSTEM

CROSS-REFERENCE TO RELATED APPLICATIONS

This application is based upon and claims the benefit of priority from Japanese Patent Application No. 2010-222804, filed on Sep. 30, 2010, the entire contents of which are incorporated herein by reference.

BACKGROUND OF THE INVENTION

1. Field of the Invention

The present invention relates to a microscope system that processes a pathology specimen image of a pathology specimen that is acquired using a microscope and relates to a distribution system that includes the microscope system.

2. Description of the Related Art

In a pathologic diagnosis, magnification observation is usually performed using a microscope on a block specimen obtained by organ harvesting or a specimen obtained by needle biopsy (pathology specimen). Because a pathology specimen is almost colorless and transparent, it is usually stained with pigment prior to the observation. Various staining methods have been proposed. Particularly for pathology specimens, hematoxylin-eosin staining (hereinafter, "HE staining") is used as the standard. Two pigments are used: hematoxylin, which is bruise blue, and eosin, which is red.

A pathology specimen is observed by the naked eye of an observer. In addition, the pathology specimen is also observed by capturing a multiband image and displaying it on a screen. In this case, the content of the pigment with which the specimen is stained is calculated (estimated) from the pixel values of the captured multiband image (pathology specimen image), the color of the image is appropriately corrected according to the calculated pigment content, and then an RGB image of the specimen for observation (specimen RGB image) is composited and then displayed on the screen.

Conventionally, smaller medical facilities that do not have the equipment for staining a pathology specimen request medical facilities that do have such equipment to stain a pathology specimen. Usually, the requested medical facility stains the pathology specimen, captures a multiband image of the pathology specimen, calculates the content of pigment from the acquired pathology specimen image, and saves the pigment content. For example, in response to a request from a requesting medical facility, the requested medical facility performs data communications with the requesting medical facility in order to transmit data on the pigment content. Then, the requesting medical facility reproduces the pixel values of the pathology specimen image from the received data on the pigment content, composites a specimen RGB image based on the reproduced pixel values of the pathology specimen image, and displays the specimen RGB image on the screen. In this manner, the pathology specimen is observed.

A technology for processing an image acquired using a microscope is known in which the quality of a charged particle image of a sample, which is acquired by a charged particle microscope device, is improved by using the shape of a pattern formed on the sample and the sample properties (Japanese Laid-open Patent Publication No. 2009-245674).

SUMMARY OF THE INVENTION

A microscope system according to an aspect of the present invention includes an image acquiring unit that acquires a pathology specimen image of a pathology specimen by using a microscope, the pathology specimen being stained with a predetermined pigment; a pigment content converter that converts, by using properties of the pigment, a pixel value of the pathology specimen image to pigment content of the pigment at a corresponding point on the pathology specimen; a property information adding unit that generates conversion image data by adding the properties of the pigment, which is used for the conversion, to the pigment content of each pixel converted by the pixel content converter; and a transmitter that transmits the conversion image data to an external device.

A distribution system according to another aspect of the present invention includes a microscope system; and a terminal device that is connected to the microscope system via a network. The microscope system includes an image acquiring unit that acquires a pathology specimen image of a pathology specimen by using a microscope, the pathology specimen being stained with a predetermined pigment; a pigment content converter that converts, by using properties of the pigment, a pixel value of the pathology specimen image to pigment content of the pigment at a corresponding point on the pathology specimen; a property information adding unit that generates conversion image data by adding the properties of the pigment, which is used for the conversion, to the pigment content of each pixel converted by the pixel content converter; and a transmitter that transmits the conversion image data to an external device. The terminal device includes a receiver that receives the conversion image data transmitted from the microscope system; and an image reproducer that reproduces the pixel value of the pathology specimen image based on the pigment content of each pixel and the properties of the pigment, the pigment content and the properties constituting the conversion image data.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described in detail below with reference to the accompanying drawings. The following embodiments do not limit the present invention. The same reference numbers denote the same or like parts throughout the drawings.

Figure 1:
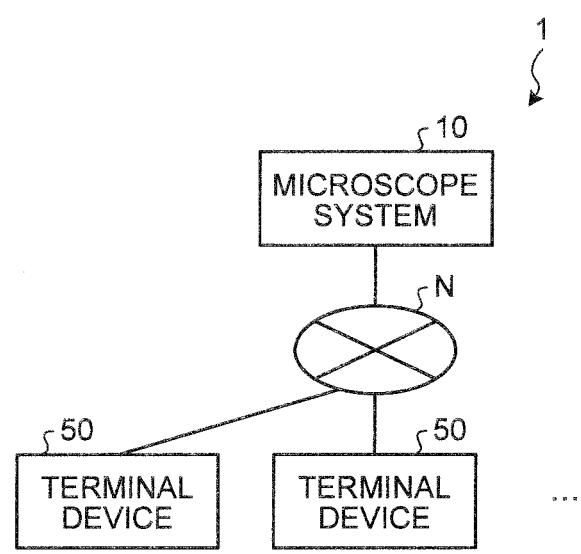
FIG. 1 is a block diagram of an example of an overall configuration of a distribution system.

FIG. 1 is a block diagram of an example of an overall configuration of a distribution system 1 according to an embodiment of the present invention. As shown in FIG. 1, the distribution system 1 includes a microscope system 10 and terminal devices 50 that function as external devices and that are connected to the microscope system 10 to communicate with the microscope system 10 via a network N. Various communication networks, such as a telecommunications network, the Internet, a LAN, a dedicated line, and an intranet, can be appropriately employed as the network N.

Figure 2:
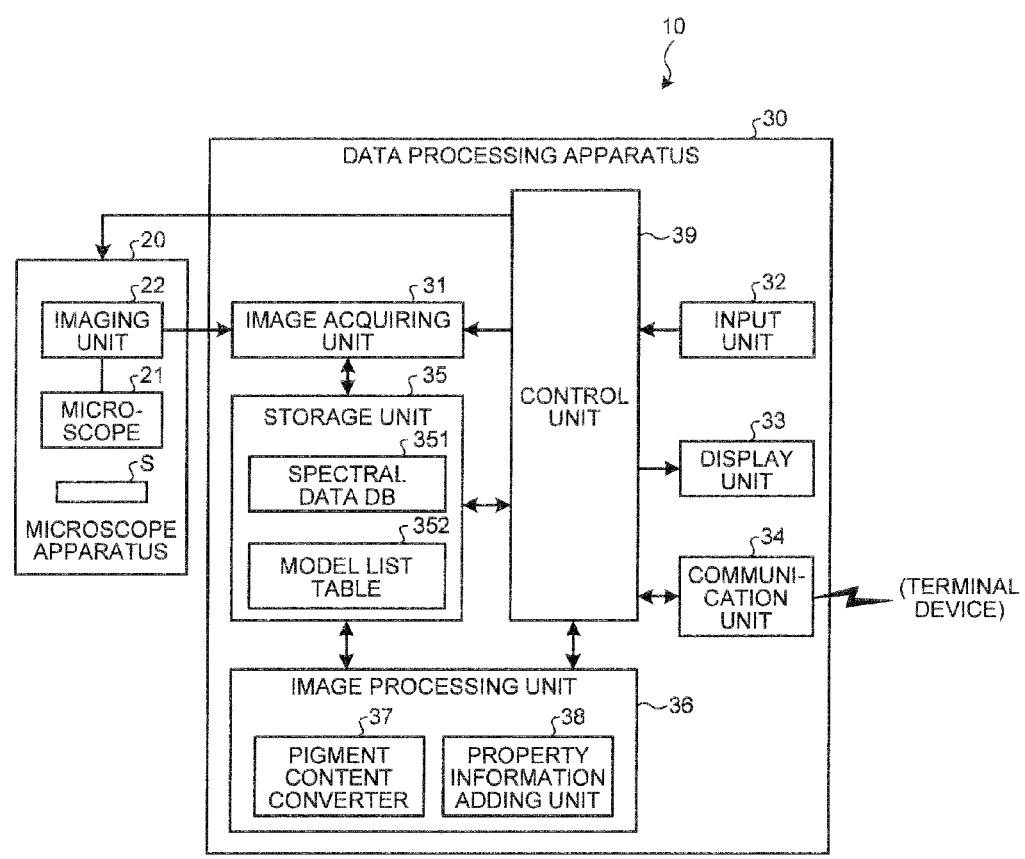
FIG. 2 is a block diagram of a configuration example of a microscope system.

FIG. 2 is a block diagram of a configuration example of the microscope system 10. As shown in FIG. 2, the microscope system 10 includes a microscope apparatus 20 and a data processing apparatus 30 that are connected such that data can be transmitted and received between them. The microscope system 10 is installed, for example, in medical facilities that have equipment for staining pathology specimens.

The microscope apparatus 20 observes a HE-stained pathology specimen S. The microscope apparatus 20 captures a multiband observation image of the pathology specimen S. The obtained observed values of pigments that are substances on the pathology specimen S, or more specifically, the image data of the multiband image of the pathology specimen S (pathology specimen image), are output to an image acquiring unit 31 of the data processing apparatus 30. The microscope apparatus 20 includes a microscope 21 and an imaging unit 22.

In the present embodiment the pathology specimen S that is, for example, H-E stained is observed. In this case, the pigment with which the pathology specimen S is stained contains, for example, three pigments: hematoxylin (pigment H), eosin (pigment E), and another staining component. Another staining component is, more specifically, eosin that stains the erythrocyte or the color of unstained erythrocyte (pigment R). The microscope system 10 converts the pixel value of each pixel of the pathology specimen image to pigment content that is the substance content of each pigment.

The microscope 21 is used to observe the pathology specimen S with transmitted light. The microscope 21 includes a light source that emits illumination light, an objective lens, an electric stage on which the pathology specimen S is placed and that moves in the plane of the optical axis direction of the objective lens and a plane orthogonal to the optical axis direction, an illuminating optical system that illuminates the pathology specimen S on the electric stage with transmitted light, and an observation optical system that operates in association with the objective lens to form an observation image of the pathology specimen S. The illumination optical system emits the illumination light from the light source to the pathology specimen S and the observation optical system forms an observation image of the pathology specimen S.

The imaging unit 22 employs, for example, the imaging method disclosed in Japanese Laid-open Patent Publication No. 07-120324 and captures a multiband observation image of the pathology specimen S while switching between a predetermined number of (for example, 16) band-pass filters with different wavelength bands of light to be transmitted by using the frame sequential method. If 16 band-pass filters are used, a pathology specimen image is obtained as a multiband image of 16 band-pass filters. For example, the imaging unit 22 includes, for example, a filter unit in which the predetermined number of band-pass filters is set in a filter wheel and the filter wheel is rotated so that each band-pass filter is selectively inserted in the optical axis of the objective lens; and an RGB camera including a CCD or CMOS imaging device. The imaging unit 22 captures a multiband observation image of the pathology specimen S, thereby acquiring a pathology specimen image. RGB cameras are often used, for example, in digital cameras. The RGB camera may be a single-chip camera in which RGB color filters are arranged as a Bayer filter on a monochrome imaging device or the RGB camera may be a triple-chip camera.

The pixel value of each pixel of image data obtained by the imaging unit 22 corresponds to the intensity of light of each wavelength band of each band-pass filter, and a pixel value (spectral data) of each wavelength band of each point (sample point) on the pathology specimen S is obtained. The sample points are each point on the pathology specimen S corresponding to each pixel point of the imaging device constituting the camera. The imaging unit 22 does not necessarily include a filter unit. Alternatively, the imaging unit 22 may capture pathology specimen images of three bands of R, G, B using the RGB camera.

The data processing apparatus 30 is realized using a general-purpose computer, such as a work station or a personal computer. The data processing apparatus 30 includes the image acquiring unit 31, an input unit 32, a display unit 33, a communication unit 34 (transmitter), a storage unit 35, an image processing unit 36, and a control unit 39 that controls each unit of the apparatus.

The image acquiring unit 31 is an interface device that inputs image data of a pathology specimen image that is captured as a multiband image by the microscope apparatus 20. The input unit 32 is realized using various input devices, such as a keyboard, a mouse, a touch panel and various switches. The input unit 32 outputs an input signal corresponding to an operation input to the control unit 39. The display unit 33 is realized using a display device, such as a LCD display, an EL display, or a CRT display. The display unit 33 displays various screens according to display signals input from the control unit 39. The communication unit 34 performs data communication with an external device via a predetermined communication line. The communication unit 34 is realized using a modem, a TA, the jack of a communication cable, and a control circuit.

The storage unit 35 is realized using information recording media including various IC memories, such as flash memories of a ROM and a RAM in which data can be updated and stored, a hard disk that is incorporated or connected via a data communication terminal, and a CD-ROM; and a reading device that reads data from the information recording media. The storage unit 35 previously stores programs for causing the microscope system 10 to operate and for realizing various functions of the microscope system 10 and stores data used during execution of the programs or the storage unit 35 temporarily stores the programs or data each time processing is performed. The storage unit 35 stores image data of a pathology specimen image (the pixel value of each pixel), which is acquired by the microscope apparatus 20 and input from the microscope apparatus 20 via the image acquiring unit 31, i.e., spectral data of each wavelength band of each pixel, and the storage unit 35 stores conversion image data obtained by signal processing on the pathology specimen image performed by the image processing unit 36. The storage unit 35 also stores spectral data DB 351 and a model list table 352.

The spectral data DB 351 is a data base (DB) that registers spectral data of each pigment (hereinafter, "pigment spectral data") according to each attribute. The spectral data are properties of pigment (here, pigment H, pigment E, and pigment R) used by a pigment content converter 37 of the image processing unit 36 to calculate the pigment content. The pigment spectral data registered in the spectral data DB 351 is prepared as, for example, light absorbance of each predetermined wavelength interval of a predetermined wavelength range from a starting wavelength to an end wavelength.

Even between pathology specimens for which the same HE staining is performed, the pigment spectral data of the pigment H, the pigment E, and the pigment R with which the pathology specimen is stained varies according to the attribute. As the attribute, for example, the sex of the subject or the type of the pathology specimen, such as the sampled organ, is taken as an example. The pigment spectral data varies also according to the attribute regarding the staining step, such as the type of staining solution used (the manufacturer of the staining solution); the combination of staining solutions used; the stained state, such as deep staining or light staining; and the environment during staining, such as the place of staining (staining facilities). For this reason, living tissue specimens with different attributes are prepared, pigment spectral data is acquired according to each attribute, and the acquired data is registered in the spectral data DB 351. Specifically, for the pigment spectral data of the pigment H and the pigment E, specimens that are individually stained (singularly-stained specimen) using the pigment H or the pigment E are prepared according to each attribute. The spectral data of the specimens is then measured using a spectrometer and absorbance at multiple sample points is obtained using the Beer-Lambert law, thereby acquiring the pigment spectral data. For pigment spectral data of the pigment R, specimens that are unstained are prepared according to each attribute and spectral data of the specimens is acquired using the microscope apparatus 20. On the basis of the image data, processing to calculate absorbance at multiple sample points by using the Beer-Lambert law is performed. Areas of erythrocyte are selected as the sample points. An average of the acquired absorbance at the sample points is calculated and the average is used as the pigment spectral data of the pigment R of the corresponding attribute.

The model list table 352 stores multiple conversion models including a conversion model that models and defines a way of converting the pixel value of each pixel of a pathology specimen image to pigment content. The types and the number of conversion models to be stored are not particularly limited. The model list table 352 stores a conversion model that contains properties of substances on the pathology specimen S as parameters and, by using the properties of the substances, represents the relation between the observed values of the substances on the pathology specimen S and the content of substances. Specifically, a conversion model based on the Beer-Lambert law is taken as an example. The conversion model based on the Beer-Lambert law contains pigment spectral data as parameters and, by using the pigment spectral data, represents the relation between the pixel value and the pigment content of the pathology specimen image according to the Beer-Lambert law.

Figure 3:
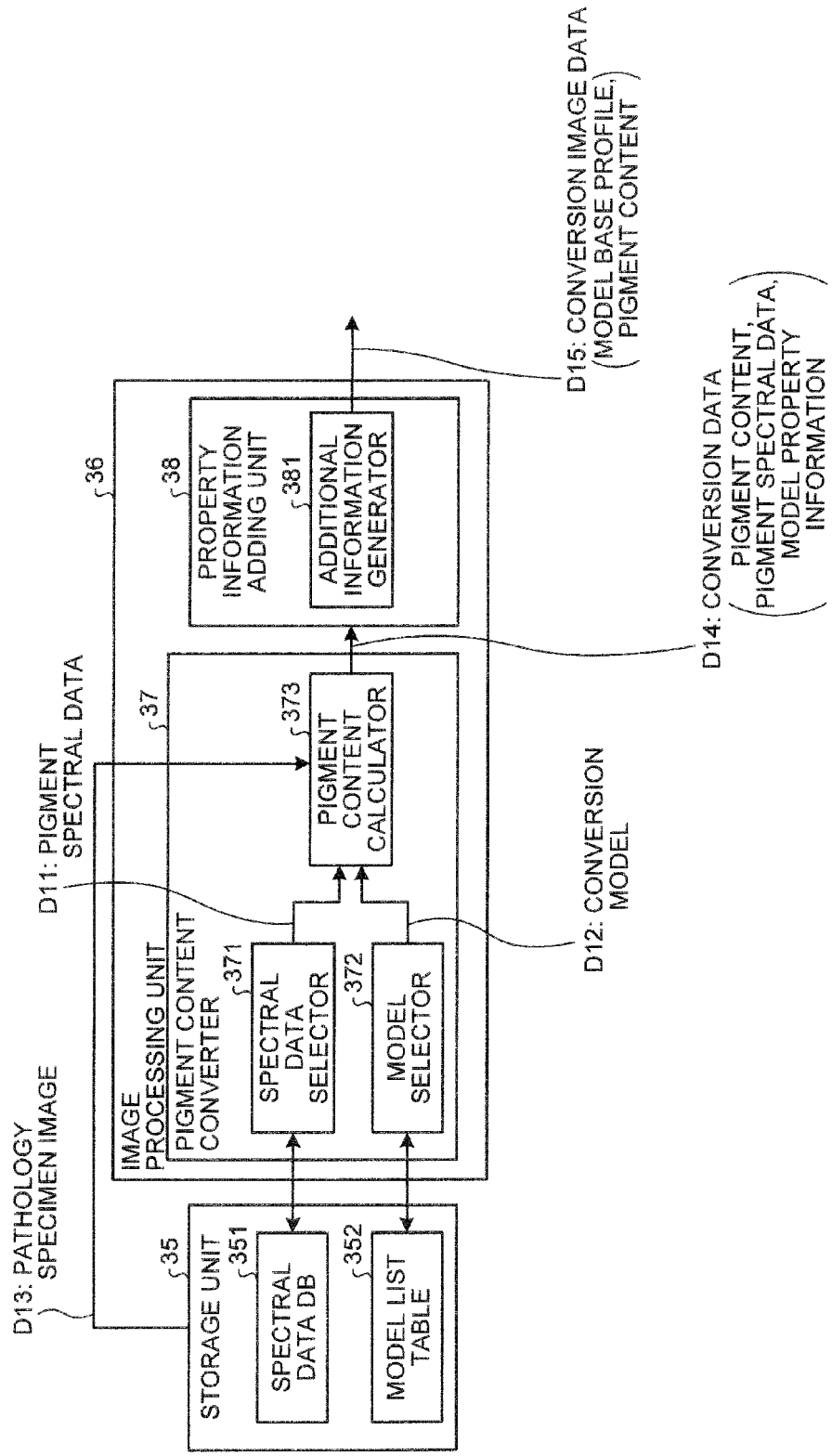
FIG. 3 is a block diagram of a configuration example of an image processing unit of a data processing apparatus.

The image processing unit 36 contains the pigment content converter 37 and a property information adding unit 38. FIG. 3 is a block diagram of a configuration example of the image processing unit 36.

The pigment content converter 37 converts a pixel value of each pixel of a pathology specimen image, i.e., the spectral data of each wavelength band, to pigment content. As shown in FIG. 3, the pigment content converter 37 includes a spectral data selector 371, a model selector 372, and a pigment content calculator 373.

The spectral data selector 371 refers to the spectral data DB 351. For example, according to a user operation, the spectral data selector 371 selects and reads pigment spectral data of the pigment H, the pigment E, and the pigment R, which is used by the pigment content calculator 373 to calculate pigment content, from the pigment spectral data of the pigment H, the pigment E, and the pigment according to each attribute registered in the spectral data DB 351. The read pigment spectral data D11 of the pigment H, the pigment E, and the pigment R is input to the pigment content calculator 373.

For example, according to a user operation, the model selector 372 selects and reads a conversion model used by the pigment content calculator 373 to calculate pigment content from the conversion models stored in the model list table 352. A read conversion model D12 is input to the pigment content calculator 373.

A pathology specimen image D13 that is input from the microscope apparatus 20 via the image acquiring unit 31 and stored in the storage unit 35 is input to the pigment content calculator 373. The pigment content calculator 373 calculates pigment content at a sample point on the pathology specimen S corresponding to each pixel on the basis of the pixel value of each pixel of the pathology specimen image (spectral data of each wavelength band of each pixel). The pigments corresponding to the conversion are the pigment H, the pigment E, and the pigment R, and the pigment content calculator 373 calculates pigment content of the pigment H, the pigment E, and the pigment R fixed to sample points corresponding to pixels of the pathology specimen image. Specifically, the pigment content calculator 373 calculates the pigment content of each pixel by converting, using pigment spectral data D11 of the pigment H, the pigment E, and the pigment R input from the spectral data selector 371, the pixel value of each pixel of the pathology specimen image D13 (spectral data of each wavelength band of each pixel) according to the conversion model D12 input from the model selector 372. The acquired data of the pigment content of the pixels is input as conversion data D14 to the property information adding unit 38 in association with the specifying information, such as a model name, (hereinafter, "model specifying information") that specifies the conversion model used for the conversion (calculation).

The property information adding unit 38 adds, to the pigment content of each pixel input from the pigment content calculator 373, a model base profile as additional information containing the pigment spectral data of the pigment H, the pigment E, and the pigment R used for the conversion (calculation). The property information adding unit 38 includes an additional information generator 381 that generates the model base profile. In the model base profile, the description is given in a predetermined format of the relation between the pigment content, which is obtained by converting the pixel value of each pixel of the pathology specimen image, and the pigment spectral data of the pigment H, the pigment E, and the pigment R used for the conversion (calculation). The model base profile generated by the additional information generator 381 is added to the pigment content of each pixel and then the resultant data is output as conversion image data D15.

The control unit 39 controls the entire operation of the microscope system 10 by, according to input signals input from the input unit 32 or the programs and data stored in the storage unit 35, transferring instructions or data to each unit of the microscope apparatus 20 or transferring instructions or data to each unit of the data processing apparatus 30.

Figure 4:
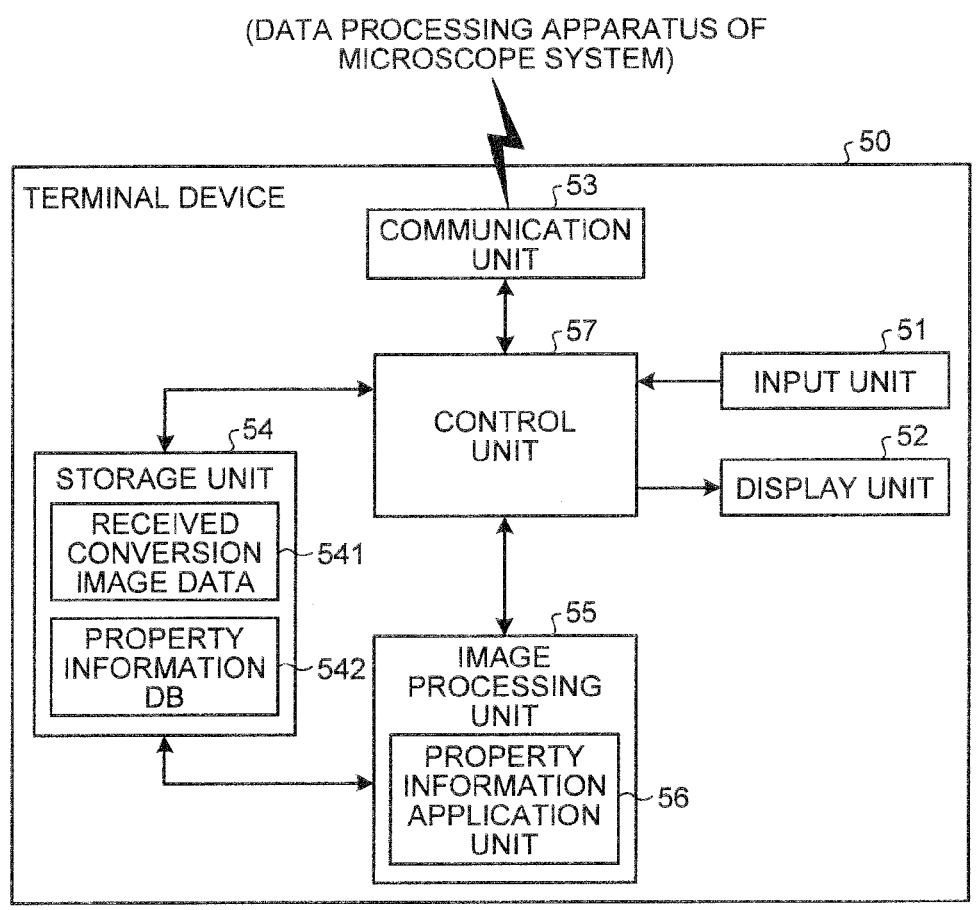
FIG. 4 is a block diagram of a configuration example of a terminal device.

The configuration of the terminal device 50 will be described below. The terminal device 50 is, for example, used by a user, such as a pathologist, to perform a diagnosis. The terminal device 50 is installed in a medical facility where a pathologist who diagnoses the observed pathology specimen S by using the microscope system 10 works. FIG. 4 is a block diagram of a configuration example of the terminal device 50.

The terminal device 50 is realized using a general-purpose computer, such as a work station or a personal computer. As shown in FIG. 4, the terminal device 50 includes an input unit 51, a display unit 52, a communication unit 53 (receiver), a storage unit 54, an image processing unit 55, and a control unit 57 that controls each unit of the device.

The input unit 51 is realized using various input devices, such as a keyboard, a mouse, a touch panel and various switches. The input unit 51 outputs input signals according to operation inputs to the control unit 57. The display unit 52 is realized using a display device, such as a LCD display, an EL display, or a CRT display. The display unit 52 displays various screens based on display signals that are input from the control unit 57. The communication unit 53 performs data communications with an external device via a predetermined communication line. The communication unit 53 is realized using a modem, a TA, a connector of a communication cable, and a control circuit.

The storage unit 54 is realized using information recording media including various IC memories, such as flash memories of a ROM and a RAM in which data can be updated and stored, a hard disk that is incorporated or connected via a data communication terminal, and a CD-ROM; and a reading device that reads data from the information recording media. The storage unit 54 previously stores programs for causing the terminal device 50 to operate and for realizing various functions of the terminal device 50 and stores data used during execution of the programs or the storage unit 54 temporarily stores the programs or data each time processing is performed. For example, the storage unit 54 stores data of the multiple conversion models (for example, the conversion model represented by Equation (1) described later) similar to the model list table 352 stored in the storage unit 35 of the microscope system 10. The storage unit 54 also stores received conversion image data 541 and property information DB 542.

The received conversion image data 541 stores conversion image data transmitted from the microscope system 10. The property information DB 542 is a database (DB) that registers property information applicable to the pigment content of each pixel constituting the conversion image data. The property information that is registered in the property information DB 542 includes, for example, property information that specifies a predetermined color for the display color of a predetermined component of the pathology specimen.

Figure 5:
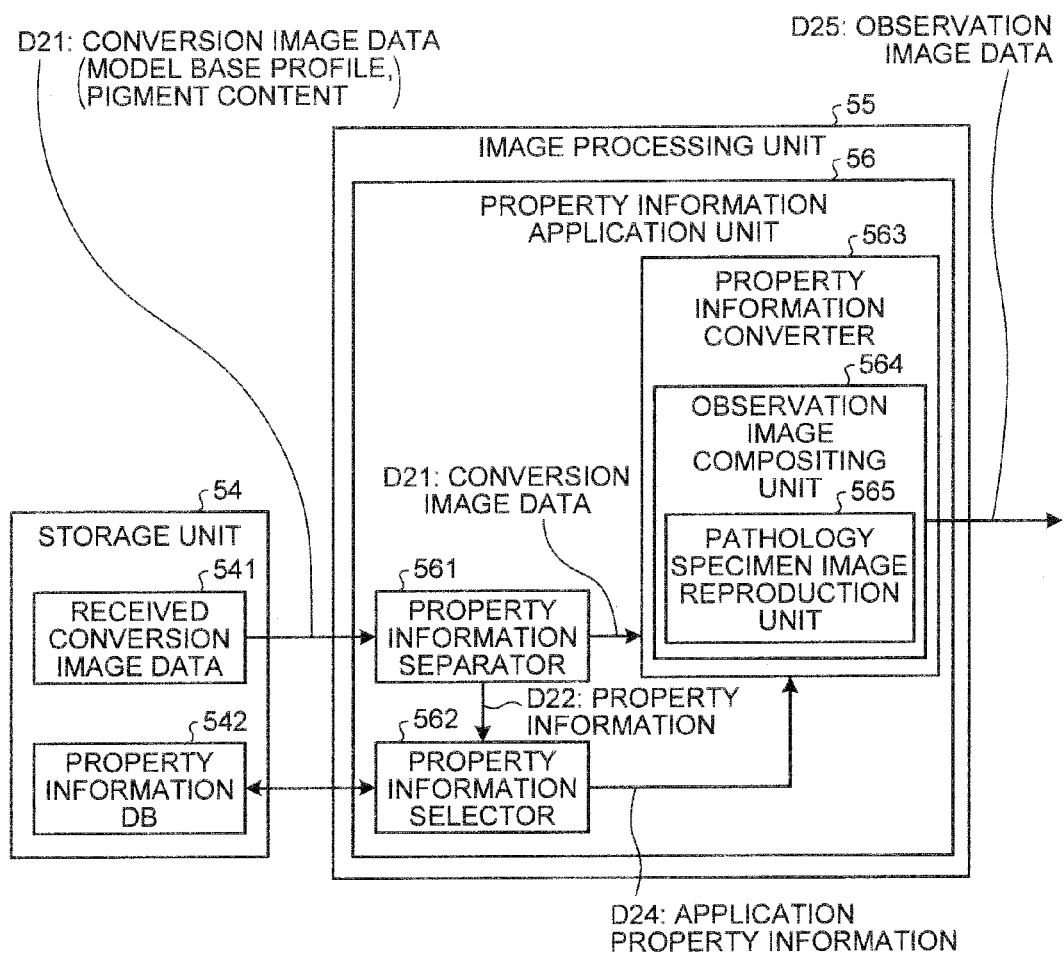
FIG. 5 is a block diagram of a configuration example of an image processing unit of the terminal device.

The image processing unit 55 includes a property information application unit 56. The property information application unit 56 composites an observation image of the pathology specimen S according to the pigment content of the conversion image data transmitted from the microscope system 10. FIG. 5 is a block diagram of a configuration example of the image processing unit 55. As shown in FIG. 5, the property information application unit 56 includes a property information separator 561, a property information selector 562, and a property information converter 563.

The property information separator 561 refers to the received conversion image data 541 of the storage unit 54, reads the conversion image data D21 transmitted from the microscope system 10, and separates the property information. The conversion image data D21 is obtained by adding the model base profile to the pigment content of each pixel. The property information separator 561 separates the property information contained in the model base profile (property information D34 in FIG. 7 described below) by extracting it. The separated property information D22 is input to the property information selector 562. The conversion image data D21 read from the storage unit 54 by the property information separator 561 is directly input to the property information converter 563.

The property information selector 562 selects property information used in processing performed by the property information converter 563. For example, the property information selector 562 selects the property information D22 input from the property information separator 561 or one type of the property information registered in the property information DB 542 according to, for example, a user operation. The selected property information is input to the property information converter 563 as application property information D24.

The property information converter 563 includes an observation image compositing unit 564. The observation image compositing unit 564 composites an observation image based on the pigment content of each pixel of the conversion image data D21, which is input from the property information selector 562, and outputs the observed image as observation image data D25. The observation image compositing unit 564 includes a pathology specimen image reproduction unit 565.

When the application property information D24 selected by the property information selector 562 and input from the property information selector 562 is the property information D22 separated by the property information separator 561 from the conversion image data D21, the pathology specimen image reproduction unit 565 reproduces the pixel value of each pixel of the pathology specimen image. Specifically, the pathology specimen image reproduction unit 565 uses the property information D22 (the pigment spectral data of the pigment H, the pigment E, and the pigment R contained in the model base profile of the conversion image data D21), which is the application property information D24, and converts the pigment content of each pixel to the pixel value of each pixel of the pathology specimen image according to the conversion model specified by the model specifying information (corresponding to the model property information D32 in FIG. 7) contained in the model base profile of the conversion image data D21.

The control unit 57 generally controls the overall operation of the terminal device 50 by transferring instructions and data to each unit of the terminal device 50 according to input signals input from the input unit 51 and the programs or data stored in the storage unit 54.

A specific procedure of processing performed by the distribution system 1 will be described below. First, conversion image data generation processing performed by the microscope system 10 will be described with reference to FIG. 6.

Figure 6:
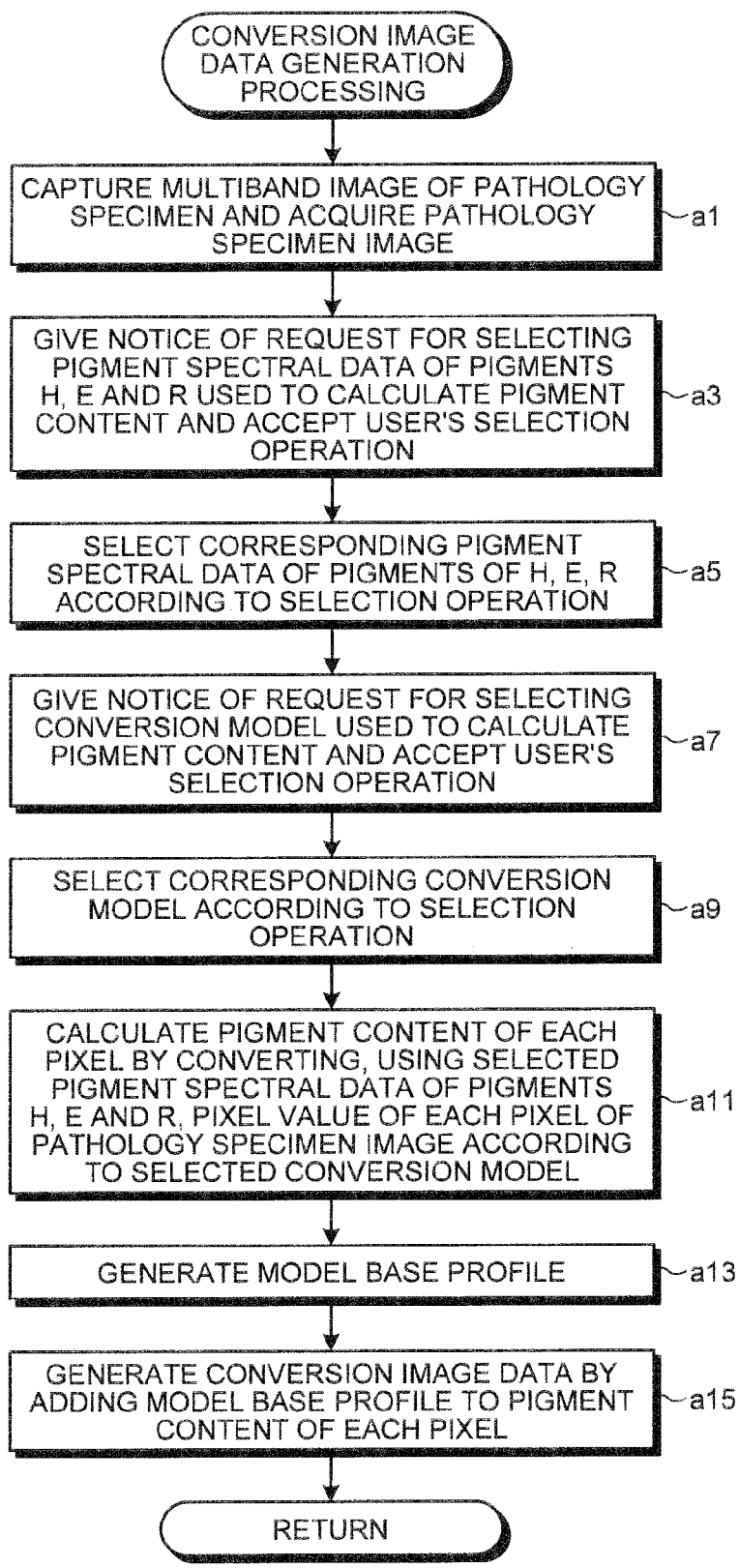
FIG. 6 is a flowchart of a detailed procedure of conversion image data generation processing performed by the microscope system.

As shown in FIG. 6, in the conversion image data generation processing, first, the control unit 39 of the data processing apparatus 30 controls the operation of the microscope apparatus 20 such that it captures a multiband image of the pathology specimen S and thus acquires a pathology specimen image (step a1).

The control unit 39 then performs processing to display, on the display unit 33, a notice of a request for selecting pigment spectral data of the pigment H, the pigment E, and the pigment R, which is pigment spectral data used for conversion to the pigment content, and accepts a user's selection operation via the input unit 32 (step a3). For example, the control unit 39 displays a message of a request for selecting pigment spectral data of the pigment H, the pigment E, and the pigment R and performs processing to display, on the display unit 33, a notice screen on which selection boxes are arranged that present, as choices, a list of attributes according to which pigment spectral data is registered in the spectral data DB 351. The user performs an operation to select, via the input unit 32, a desired attribute that meets the pathology specimen S to be observed, such as the staining facility where the pathology specimen S to be observed is made. If the pigment spectral data that fits the attribute of the pathology specimen S is selected as pigment spectral data used for conversion to the pigment content, the accuracy in calculating the pigment content at the following step a11 improves.

In response to the user's selection operation, the spectral data selector 371 of the image processing unit 36 selects and reads corresponding pigment spectral data of the pigment H, the pigment E, and the pigment R from the spectral data DB 351 according to the selection operation accepted at step a3 (step a5).

The control unit 39 then performs processing to display, on the display unit 33, a notice of a request for selecting a conversion model used for conversion to pigment content and accepts a user's selection operation via the input unit (step a7). For example, the control unit 39 displays a message of a request for selecting a conversion model and performs processing to display a notice screen on which selection boxes are arranged that present, as choices, a list of model specifying information (for example, model names) of conversion models stored in the model list table 352. The user performs an operation to select desired model specifying information via the input unit 32.

In response to the user's selection operation, the model selector 372 of the image processing unit 36 reads a corresponding conversion model from the model list table 352 according to the selection operation accepted at step a7 (step a9).

The pigment content calculator 373 then calculates pigment content of each pixel by converting, using the pigment spectral data of the pigment H, the pigment E, and the pigment R selected at step a5, the pixel value of each pixel of the pathology specimen image, which is acquired at step a1, according to the conversion model selected at step a9 (step a11). A case will be taken as an example in which model specifying information of a conversion model based on the Beer-Lambert law is selected at step a9. The conversion model based on the Beer-Lambert law is represented by the following Equation (1), where λ, denotes wavelength; f(λ) denotes spectral transmittance that can be obtained on the basis of the pixel value of each pixel of the pathology specimen image by appropriately using a well-known estimation method, such as an estimation method using main component analysis or the Wiener estimation method; $\mu_i(\lambda)$ denotes the pigment spectral data (absorbance) of the $i^{th}$ pigment; $C_i$ denotes the pigment content of the $i^{th}$ pigment; d denote the thickness of the sample; and M denotes the number of pigments for which conversion is performed. In the present embodiment, M=3 because there are three pigments for which conversion is performed: the pigment H, the pigment E, and the pigment R. At step a11, the pigment content of the pigment H, the pigment E, and the pigment R is calculated using the following Equation (1).

$$f(\lambda) = \exp\left[-\sum_{i=1}^{M} \mu_i(\lambda) C_i d\right] \quad (1)$$

Figure 7:
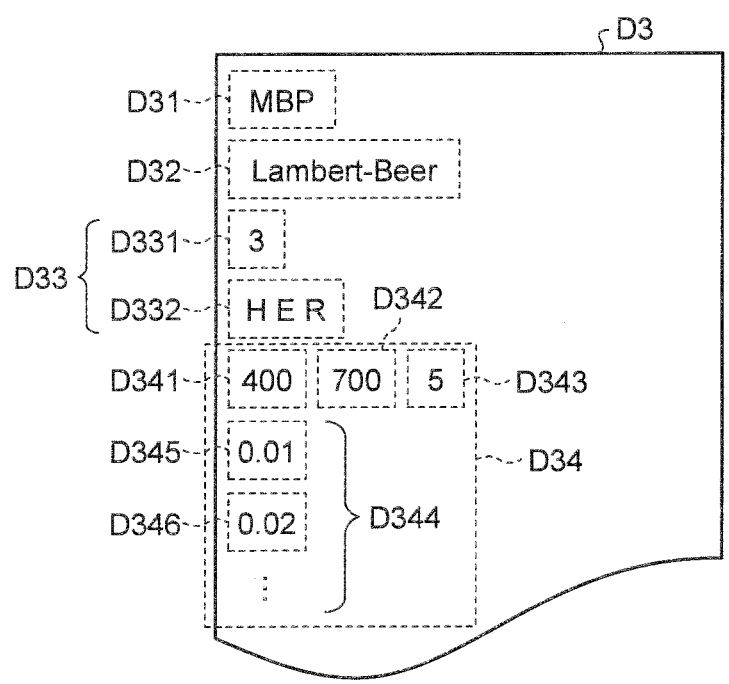
FIG. 7 is a diagram showing a format example of a model base profile.

The additional information generator 381 then generates a model base profile (step a13). FIG. 7 is a diagram showing a format example of a model base profile D3. As shown in FIG. 7, the model base profile D3 contains header information D31, model property information D32, pigment information D33 that relates to the pigment with which the pathology specimen S is stained, and property information D34.

The header information D31 is identification information indicating that it is a model base profile (MBP). The model property information D32 is model property information on the conversion model used for conversion to (calculation of) the pigment content. In FIG. 7, "Lambert-Beer" that is the model property information on the above-described conversion model based on the Beer-Lambert law is set. The pigment information D33 contains the number of pigments D331 and the type of pigment D332. In the present embodiment, the pigment for which conversion is performed includes the pigment H, the pigment E, and the pigment R and thus "3" is set as the number of pigments D331 and "H E R" is set as the type of pigment. The property information D34 contains a starting wavelength D341 and an end wavelength D342 of the pigment spectral data used for conversion to (calculation of) the pigment content, a wavelength interval D343, and pigment spectral data D344. In the pigment spectral data D344, values of absorbance D345, D346 . . . of each wavelength interval D343 from the starting wavelength D341 to the end wavelength D342 are sequentially listed. Specifically, in the example of FIG. 7, the value D345 corresponds to the absorbance of 400 nm that is the starting wavelength D341 and the value D346 corresponds to the absorbance of 405 nm.

As shown in FIG. 6, the property information adding unit 38 then adds the model base profile, which is generated at step a13, to the pigment content of each pixel, thereby generating conversion image data (step a15). The generated conversion image data is stored and saved, in the storage unit 35, in association with the attribute information on the pathology specimen S to be observed and with the specimen identification information allocated to the pathology specimen S. In response to a request from the terminal device 50, the conversion image data is transmitted to the terminal device 50.

Figure 8:
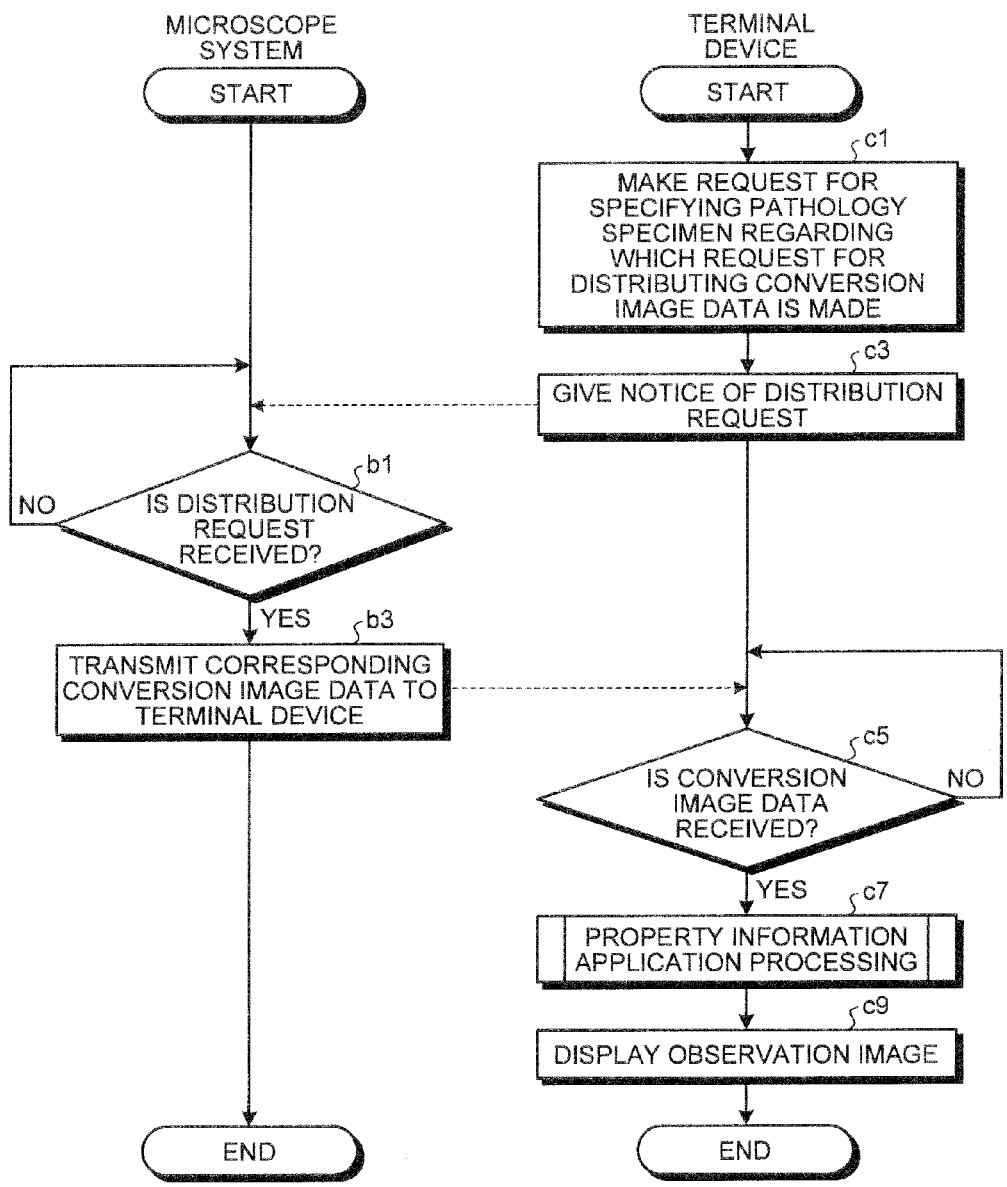
FIG. 8 is a flowchart of a procedure of processing performed by the microscope system and the terminal device.

With reference to FIG. 8, a description will be given of a procedure of processing to transmit the conversion image data, which is generated by the microscope system 10 as described above, to the terminal device 50 and receive it from the terminal device 50. In the distribution system 1, the microscope system 10 and the terminal device 50 perform data communications at arbitrary timing and the terminal device 50 acquires the conversion image data of the demanded pathology specimen S, for example, the pathology specimen S that the user who operates the terminal device 50, such as a pathologist, previously requested a medical facility where the microscope system 10 is installed to generate.

As shown in FIG. 8, to transmit or receive conversion image data, first, according to a user's operation, the display unit 52 of the terminal device 50 performs processing to display, on the display unit 52, a notice of a request for specifying a pathology specimen regarding which a request for distributing conversion image data is made and the terminal device 50 accepts a user's selection operation via the input unit 51 (step c1). For example, the control unit 57 displays a message of a request for specifying a pathology specimen and performs processing to display, on the display unit 52, a notice screen on which input boxes for inputting specimen identification information that can specify a desired pathology specimen are arranged. The user performs an operation to specify specimen identification information on the desired pathology specimen via the input unit 51.

In response to the user's specifying operation, the control unit 57 performs processing to notify the microscope system 10 of the input specimen identification information and the request for distributing the conversion image data via the communication unit 53 (step c3). The terminal device 50 then enters a standby state until it receives the conversion image data from the microscope system 10 (NO at step c5).

Regarding transmission and reception of the conversion image data, the microscope system 10 is in the standby state until it receives a notice of a distribution request from the terminal device 50 (NO at step b1). When the microscope system 10 receives a notice of a distribution request from the terminal device 50 via the communication unit 34 (YES at step b1), the control unit 39 reads corresponding conversion image data from the storage unit 35 according to the specimen identification information received together with the notice of the distribution request and the control unit 39 transmits the conversion image data to the terminal device 50 via the communication unit 34 (step b3).

Figure 9:
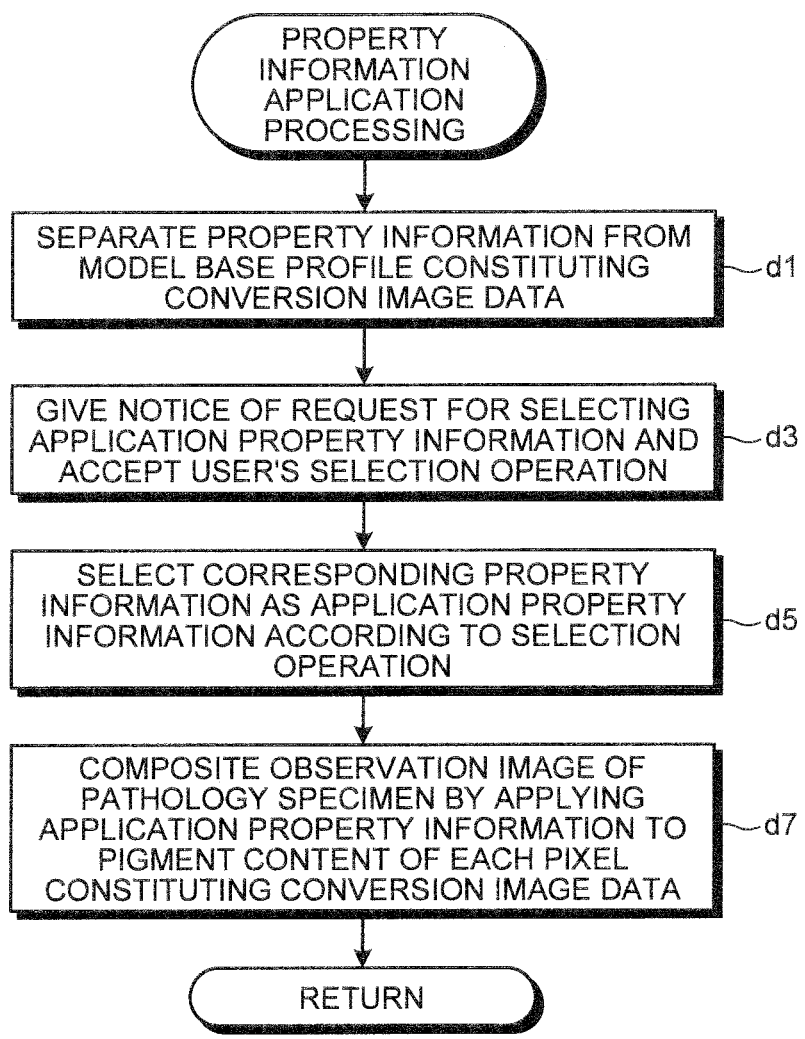
FIG. 9 is a flowchart of a detailed procedure of property information application processing performed by the terminal device.

Upon receiving the conversion image data transmitted from the microscope system 10 via the communication unit 53 (YES at step c5), the terminal device 50 enters the property information application processing (step c7). Prior to the property information application processing, the control unit 57 stores the received conversion image data in the storage unit 54 as received conversion image data. FIG. 9 is a flowchart of a detailed procedure of the property information application processing.

As shown in FIG. 9, in the property information application processing, first, the property information separator 561 of the property information application unit 56 of the image processing unit 55 reads the conversion image data, which is received at step c5 in FIG. 8 and stored as the received conversion image data 541 in the storage unit 54, and the property information separator 561 separates the property information from the model base profile constituting the conversion image data (step d1).

The control unit 57 then performs processing to display, on the display unit 52, a notice of a request for selecting application property information to be applied to the pigment content of each pixel constituting the conversion image data and the control unit 57 accepts a user's selection operation via the input unit 51 (step d3). For example, the control unit 57 displays a message of a request for selecting application property information and performs processing to display, on the display unit 52, a notice screen on which selection boxes are arranged that present, as choices, the property information separated at step d1 and the property information registered in the property information DB 542. The user performs an operation to select desired application property information via the input unit 51.

In response to the user's selection operation, according to the selection operation accepted at step d3, the property information selector 562 of the image processing unit 55 selects, as application property information, the property information separated at step d1 or reads corresponding property information from the property information DB 542 and selects the property information as application property information (step d5).

There are multiple types of imaging methods for a case in which a pathological specimen is imaged and displayed on a screen and the pathology specimen is observed and diagnosed on the screen. Types of image used for diagnosis include, in addition to a specimen RGB image described as the background art, for example, a pigment content image, a multi-stained separation image, and a digital stained image. These images are obtained by processing the pathology specimen image. The type of an image used for a diagnosis varies depending on the pathologist. In other words, while some pathologists prefer to observe and diagnose an RGB image, some pathologists prefer to observe and diagnose a digital stained image. At step d5, property information used to composite an image of the type preferred by the pathologist of the terminal device 50 is selected as application property information. Thus, a user's operation for selecting the type of observation image may be accepted at step d3 and application property information corresponding to the type of observation image selected at step d3 may be selected at step d5.

A specimen RGB image, a pigment content image, a multi-stained separation image, and a digital stained image will be briefly described. A specimen RGB image is composited by obtaining the pixel value of each pixel of the pathology specimen image, i.e., obtaining spectral transmittance of each pixel from the spectral data of each wavelength of each pixel and by converting the spectral transmittance to RGB values. The specimen RGB image can be composited using a well-known method. When compositing a specimen RGB image as an observation image, it is necessary to reproduce the pixel values of the pathology specimen image from the pixel content of each pixel; therefore, when compositing a specimen RGB image, the property information separated at step d1 is selected as application property information at step d5.

The pigment content image is an image that is composited by selectively using one or some of the pigment H, the pigment E, and the pigment R with which the pathology specimen is stained. The pigment content image can be composited using a well-known method. The procedure of the processing will be briefly described. For example, when compositing a pigment content image of the pigment H, only the pigment content of the pigment H is extracted and used among the pigment content of the pigment H, the pigment E, and the pigment R constituting the pigment of each pixel, and an image representing the shading (H pigment content image) is composited. When compositing a pigment content image of the pigment E, only the pigment content of the pigment E is extracted and used and an image representing the shading (E pigment content image) is composited. When compositing such a pigment content image as an observation image, only the pigment content of a corresponding pigment (for example, the pigment H/pigment E) is extracted and selected as the application property information from the property information separated at step d1. At the following step d7, by using the application property information, a pigment content image of the corresponding pigment is composited as an observation image.

A multi-stained separation image is used to observe a pathological specimen that is multi-stained by using multiple staining methods, for example, a pathological specimen that is not only HE-stained but also immunostained. Conventionally, target molecules of a HE-stained pathology specimen are signed by coloring them using, for example, a DAB reaction (by staining them with a pigment DAB), and a multiband image of the specimen is captured to observe the pathology specimen. Alternatively, an HE-stained pathology specimen and a pathology specimen stained with the pigment H and the pigment DAB are prepared and multiband images of the respective specimens are individually captured in order to observe the pathology specimens. The multi-stained separation image is an image composited by using one or some of the pigment H, the pigment E, and the pigment DAB with which the pathology specimen is stained. The multi-stained separation image can be composited by using a well-known method. When such a pathology specimen image is observed, it is satisfactory if the data processing apparatus 30 calculates the pigment content of the pigment H, the pigment E, and the pigment DAB, with which the pathology specimen is stained, at step a11. For example, a multi-stained separation image representing the state stained with the pigment H and the pigment E is composited by extracting and using only the pigment content of the pigment H and the pigment E from the pigment content of the pigment H, the pigment E, and the pigment DAB constituting the pigment content of each pixel, and by converting the pigment content to RGB values in the same manner as that for compositing a specimen RGB image. For example, a multi-stained separation image representing the state stained with the pigment H and the pigment DAB is composited by extracting and using only the pigment content of the pigment H and the pigment DAB from the pigment content of the pigment H, the pigment E, and the pigment DAB constituting the pigment content of each pixel, and by converting the pigment content to RGB values in the same manner as that for compositing a specimen RGB image. When compositing a multi-stained separation image as an observation image, only the pigment content of desired pigment (for example, the pigment H+the pigment E/the pigment E+the pigment DAB) is extracted and selected as application property information at step d5 from the property information separated at step d1. At the following step d7, a multi-stained separation image of the corresponding pigments is composited as an observation image by using the application property information.

A digital stained image is an image in which desired components of a pathology specimen, such as the cell nuclei, fibers, and blood vessels, are emphasized and displayed as if they are specially stained. The digital stained image is composited using a well-known method. The procedure of the processing will be briefly described. For example, the specimen RGB image described above is composited and an area of each component is extracted according to the pigment content of each pixel. By replacing the pixel values of the pixels constituting the extracted area of each component in the RGB image with the display color of each component, an image is composited in which each component in the specimen RGB image is emphasized and displayed such that each component can be distinguished from other components. For example, Masson trichrome (MT) staining for selectively staining fibers is well known and is performed to determine to which degree the liver becomes fibrotic. In Masson trichrome staining, the fibers are stained with blue. In the embodiment, the HE-stained pathology specimen S is observed. In order to composite, as an observation image, a digital stained image representing the state stained by Masson trichrome staining according to the conversion image data transmitted from the microscope system 10, it is necessary to reproduce the pixel values of the pathology specimen image from the pigment content of each pixel. It is also necessary to specify the display color (for example, blue) of the component (for example, fibers) of which display color is replaced. Thus, at step d5, the property information specifying blue as the display color of the fiber area is read and acquired from the property information DB 542 and the acquired property information and the property information separated at step d1 are both selected as the application property information.

In this case, at the following step d7, an observation image is composited by calculating, using the property information separated at step d1 from the application property information, the pixel value of each pixel of the pathology specimen image from the pigment content of each pixel constituting the conversion image data as described below; by extracting the pixels of the fiber area according to the pixel content of each pixel; and by replacing the display color of the pixels with blue by using the property information of the application property information read and acquired from the property information DB 542.

The observation image compositing unit 564 of the property information converter 563 composites an observation image of the pathology specimen by applying the selected application property information, which is selected at step d5, to the pigment content of each pixel (step d7). When the application property information is the property information separated at step d1, the pathology specimen image reproduction unit 565 performs processing to reproduce the pixel values of the pathology specimen image according to the pigment content of each pixel constituting the conversion image data. Specifically, the pathology specimen image reproduction unit 565 calculates the pixel value of each pixel of the pathology specimen image by converting, using the pigment spectral data of the pigment H, the pigment E, and the pigment R that is the application property information, the pigment content of each pixel according to the conversion model specified by the model specifying information contained in the model base profile. For example, if the model specifying information of the model base profile is the above-described conversion model based on the Beer-Lambert law, the pixel value of each pixel is calculated from the pixel content of each pixel of the pigment H, the pigment E, and the pigment R.

Once the observation image is composited as described above, the property information application processing is ended and the processing returns to step c7 in FIG. 8 and goes to step c9. At step c9, the control unit 57 performs processing to display the observation image, which is composited at step d7 in FIG. 9, on the display unit 52.

As described above, in the distribution system 1 of the present embodiment, the microscope system 10 converts the pixel value of each pixel of the pathology specimen image to pigment content of each pixel by using the pigment spectral data of the pigment H, the pigment E, and the pigment R according to the conversion model representing the relation between the pixel value and the pigment content of the pathology specimen image on the basis of the Beer-Lambert law. The microscope system 10 generates conversion image data by adding, to the pigment content of each pixel, the model base profile containing the property information, which is the pigment spectral data of the pigment H, the pigment E, and the pigment R and the model property information of the conversion model that are used for conversion to (calculation of) the pigment content. The microscope system 10 stores and saves the conversion image data in the storage unit 35 and transmits the conversion image data to the terminal device 50 at arbitrary timing. The terminal device 50 separates the property information from the model base profile constituting the conversion image data and uses the property information. The terminal device 50 converts the pigment content of each pixel constituting the conversion image data to the pixel value of each pixel of the pathology specimen image according to the conversion model specified by the model specifying information. Accordingly, the pigment content obtained by converting the pigment value of the pathology specimen image can be transmitted as data that can be properly reproduced to the pixel values of the pathology specimen image.

Furthermore, the pixel value of the pathology specimen image is converted to pigment content according to the conversion model that contains, as parameters, the pigment spectral data and in which the relation between the pixel value and the pigment content of the pathology specimen image is represented by using the pigment spectral data on the basis of the Beer-Lambert law. Accordingly, transmission of only the converted pigment content of each pixel and the pigment spectral data used for the conversion to the terminal device 50 allows the terminal device 50 to accurately reproduce the pixel values of the pathology specimen image, so that the terminal device 50 can properly analyze the pathology specimen S.

First Modification

Figure 10:
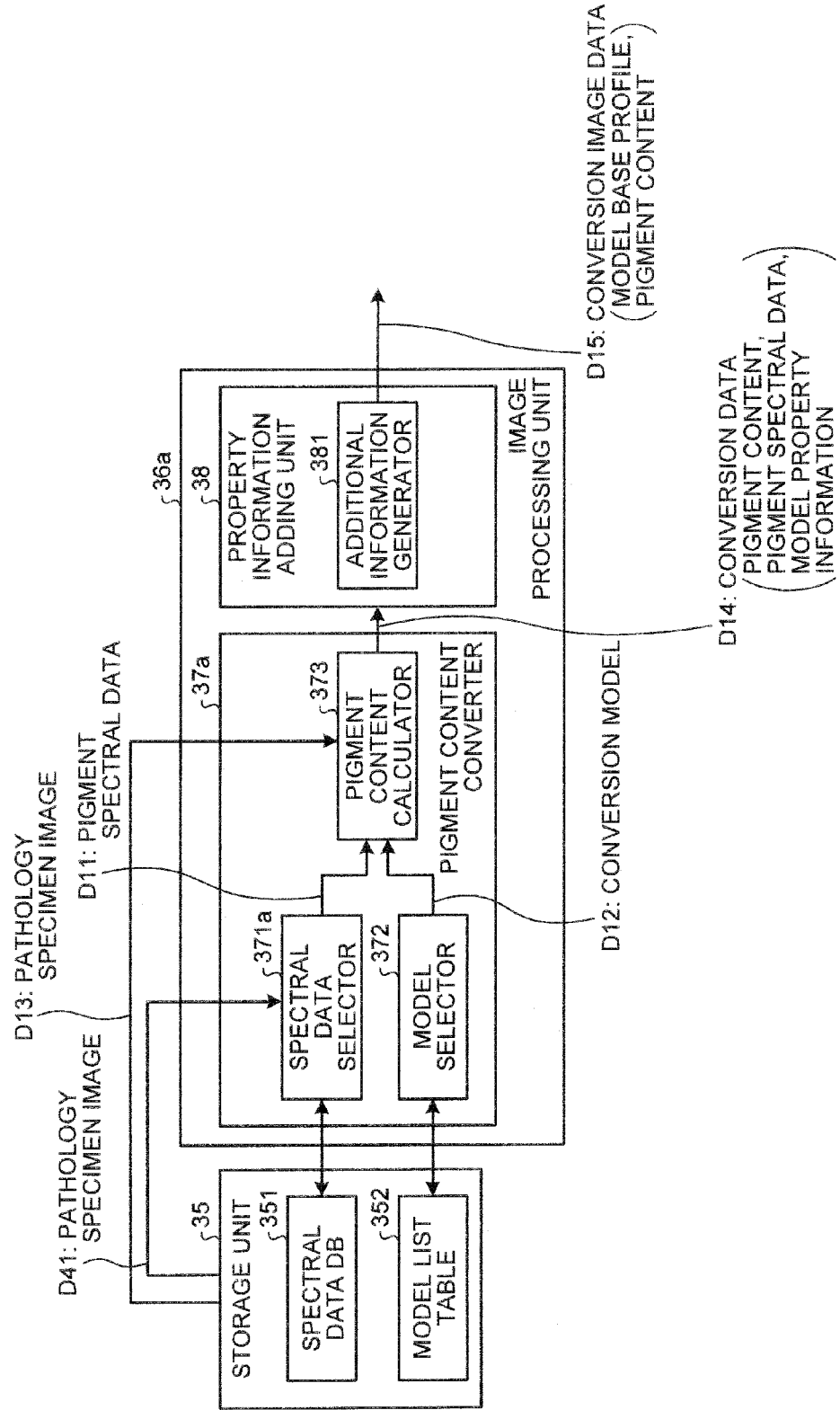
FIG. 10 is a block diagram of a configuration example of an image processing unit of a data processing apparatus of a first modification.

FIG. 10 is a block diagram of a configuration example of an image processing unit 36a of a data processing apparatus constituting a microscope system according to a first modification. The same or like parts as those of the above-described embodiment are denoted by the same reference numbers. As shown in FIG. 10, the image processing unit 36a of the first modification includes a pigment content converter 37a and the property information adding unit 38. The pigment content converter 37a includes a spectral data selector 371a, the model selector 372, and the pigment content calculator 373.

In the first modification, a pathology specimen image D41 that is input from the microscope apparatus 20 via the image acquiring unit 31 and stored in the storage unit 35 is input to the spectral data selector 371a. On the basis of the input pathology specimen image D41, the spectral data selector 371a automatically selects and reads pigment spectral data of the pigment H, the pigment E, and the pigment R that is optimum in order to convert the pixel value of each pixel of the pathology specimen image D41 to the pigment content from the pigment spectral data of the pigment H, the pigment E, and the pigment R of each attribute registered in the spectral data DB 351.

Specifically, j with which the difference from f ($\lambda$) is the minimum is acquired by using the following Equation (2) and the following Expression (3). Equation (2) corresponds to Equation (1) for $\mu^j_i$ ($\lambda$) and $f^j$ ($\lambda$) where $\mu^j_i$ ($\lambda$) denotes the pigment spectral data of the $j^{th}$ pigments H, E, R, which is registered in the spectral data DB and $f^j$ ($\lambda$) denotes spectral transmittance for the $j^{th}$ pigments H, E, R. The pigment spectral data of the acquired $j^{th}$ pigments H, E, and R is selected and read from the spectral data DB 351. Here, the pigment spectral data of the pigment H, the pigment spectral data of the pigment E, and the pigment spectral data of the pigment R are dealt with as a set of data. Alternatively a configuration may be employed in which the pigment spectral data of the pigment H, the pigment spectral data of the pigment E, and the pigment spectral data of the pigment R are individually selected.

$$f^j(\lambda) = \exp\left[-\sum_{i=1}^M \mu^j_i(\lambda) C_i d\right] \quad (2)$$

$$\int [f(\lambda) - f^j(\lambda)]^2 d\lambda \to \min \quad (3)$$

Second Modification

Figure 11:
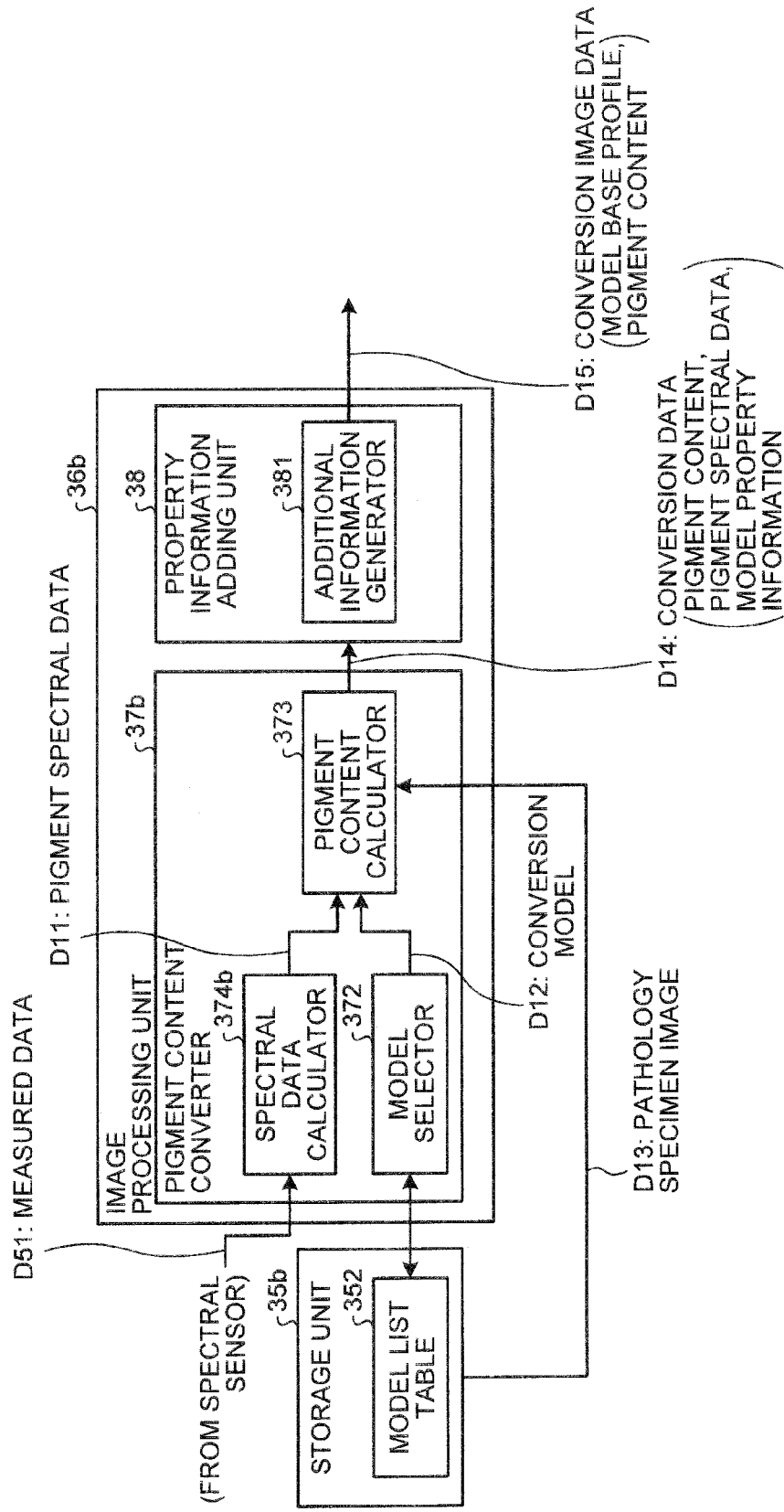
FIG. 11 is a block diagram of a configuration example of an image processing unit of a data processing apparatus of a second modification.

FIG. 11 is a block diagram of a configuration example of an image processing unit 36b of a data processing apparatus constituting a microscope system of a second modification. The same or like parts as those of the above-described embodiment are denoted by the same reference numbers. As shown in FIG. 11, the image processing unit 36b of the second modification includes a pigment content converter 37b and the property information adding unit 38. The pigment content converter 37b includes a spectral data calculator 374b, the model selector 372, and the pigment content calculator 373.

In the microscope system of the second modification, the microscope apparatus includes a spectral sensor. Thus, the spectral sensor can measure spectral data of a pathology specimen at the same time as the imaging unit captures an image of the pathology specimen. In the second modification, spectral data D51 measured by the spectral sensor (measured data) is input to the spectral data calculator 374b. The spectral data calculator 374b calculates pigment spectral data of the pigment H, the pigment E, and the pigment R on the basis of the measured data D51 input from the spectral sensor. The pigment spectral data of the pigment H, the pigment E, and the pigment R is calculated by appropriately using a well-known method. In the second modification, because it is unnecessary to prepare beforehand the spectral data of the pigment H, the pigment E, and the pigment R, a storage unit 35b of the data processing apparatus constituting the microscope system of the second modification does not need to store the spectral data DB 351 (see FIG. 2) described in the above-described embodiment.

In the above-described embodiment, the conversion model is described in one based on the Beer-Lambert law. For example, a conversion model using a dispersion model that can be used to observe an unstained pathology specimen that is not stained with any pigment can be taken as another conversion model.

Because an unstained pathology specimen is not stained with any pigment, it is difficult to confirm its characteristics by the naked eye. However, no staining process is required and thus the pathology specimen does not alter. Tissues, such as cell nuclei, cell cytoplasm, and connective tissues, are different in their structures and thus the degree of dispersion is different between the tissues. For this reason, when an unstained pathology specimen is observed, the pixel values of the pathology specimen image can be represented by using a conversion model using the dispersion model using the following Equation (4), where $\lambda$, denotes wavelength, f ($\lambda$) denotes spectral transmittance, $\mu_s$ ($\lambda$) denotes a dispersion coefficient, and d denotes the thickness of a sample.

$$f(\lambda) = \exp[-\mu_s(\lambda) d] \quad (4)$$

The conversion model represented by Equation (4) may be stored in the model list table 352, and the conversion model based on the Beer-Lambert law, which is described as an example in the above-described embodiment, and the conversion model using a dispersion model may be selectively used according to whether the pathology specimen to be observed is stained with pigment or not stained with any pigment.

As described above, according to the above-described embodiment and the modifications, the conversion image data is generated by adding the properties of the pigment used to convert the pixel value of the pathology specimen image to the pigment content, and the conversion image data can be transmitted to the external device. In this manner, the pigment content obtained by converting the pixel value of the pathology specimen image can be transmitted as data that can be appropriately reproduced to the pixel values of the pathology specimen image.

In the above-described embodiment and the modifications, descriptions are given of the cases in which the HE-stained pathology specimen is a target specimen. In addition to the HE staining, various staining methods are well known. These staining methods are generally divided into special staining and immune living tissue chemical staining. The present invention can be similarly applied to any case where a pathology specimen that is stained by any staining method is observed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microscope system comprising:
an interface device that acquires a pathology specimen image of a pathology specimen by using a microscope, the pathology specimen being stained with a predetermined pigment;
a storage unit comprising hardware that stores a data base in which a plurality of pigment spectral data are registered according to a respective attribute regarding a type of the pathology specimen;
a processor comprising hardware, the processor being configured to implement:
(a) a spectral data selector that selects a pigment spectral data of the pigment among the plurality of pigment spectral data based on the attribute corresponding to the pathology specimen image acquired by the image acquiring unit;
(b) a pigment content converter that converts, by using properties of the pigment including the pigment spectral data selected by the spectral data selector, a pixel value of the pathology specimen image to pigment content of the pigment at a corresponding point on the pathology specimen;
(c) an additional information generator that generates a model base profile containing header information, model property information, pigment information related to the pigment with which the pathology specimen is stained, and pigment property information, the model property information being a conversion model that was used to convert the pixel value of the pathology specimen image to the pigment content of the pigment; and
(d) a property information adding unit that generates conversion image data by adding the model base profile to the pigment content of each pixel converted by the pixel content converter; and
a transmitter that transmits the conversion image data to an external device.

2. A distribution system comprising:
a microscope system; and
a terminal device that is connected to the microscope system via a network, wherein
the microscope system comprises:
an interface device that acquires a pathology specimen image of a pathology specimen by using a microscope, the pathology specimen being stained with a predetermined pigment;
a storage unit comprising hardware that stores a data base in which a plurality of pigment spectral data are registered according to a respective attribute regarding a type of the pathology specimen;
a first processor comprising hardware, the first processor being configured to implement:
(a) a spectral data selector that selects a pigment spectral data of the pigment among the plurality of pigment spectral data based on the attribute corresponding to the pathology specimen image acquired by the image acquiring unit;
(b) a pigment content converter that converts, by using properties of the pigment including the pigment spectral data selected by the spectral data selector, a pixel value of the pathology specimen image to pigment content of the pigment at a corresponding point on the pathology specimen;
(c) an additional information generator that generates a model base profile containing header information, model property information, pigment information related to the pigment with which the pathology specimen is stained, and pigment property information, the model property information being a conversion model that was used to convert the pixel value of the pathology specimen image to the pigment content of the pigment; and
(d) a property information adding unit that generates conversion image data by adding the model base profile to the pigment content of each pixel converted by the pixel content converter; and
a transmitter that transmits the conversion image data to the terminal device, and
the terminal device comprises:
a receiver that receives the conversion image data transmitted from the microscope system; and
a second processor comprising hardware, the second processor being configured to implement an image reproducer that reproduces the pixel value of the pathology specimen image based on the pigment content of each pixel and the properties of the pigment, the pigment content and the properties constituting the conversion image data.

3. The distribution system according to claim 2, wherein
the pigment content converter converts, according to the conversion model, the pixel value of the pathology specimen image to the pigment content, and
the image reproducer converts the pigment content of each pixel to the pixel value of the pathology specimen image according to the conversion model.

4. The distribution system according to claim 2, wherein
the second processor is configured to implement an image compositing unit that composites an observation image based on the pixel value of the pathology specimen image that is reproduced by the image reproducer; and
wherein the terminal device further comprises a display that displays the observation image.

5. The microscope system according to claim 1, wherein
the header information is identification information indicating that the header information is the model base profile,
the pigment information is the number of pigments and a type of pigment, and
the pigment property information is a starting wavelength and an end wavelength of the pigment spectral data used for conversion of the pigment content, a wavelength interval, and the pigment spectral data in which values of absorbance of each of the wavelength interval from the starting wavelength to the end wavelength are sequentially listed.

6. The distribution system according to claim 2, wherein
the header information is identification information indicating that the header information is the model base profile,
the pigment information is the number of pigments and a type of pigment, and
the pigment property information is a starting wavelength and an end wavelength of the pigment spectral data used for conversion of the pigment content, a wavelength interval, and the pigment spectral data in which values of absorbance of each of the wavelength interval from the starting wavelength to the end wavelength are sequentially listed.

7. The distribution system according to claim 2, wherein the pigment content converter converts, according to the conversion model, the pixel value of the pathology specimen image to the pigment content;

wherein the image reproducer converts the pigment content of each pixel to the pixel value of the pathology specimen image according to the conversion model;

wherein the second processor is configured to implement an image compositing unit that composites an observation image based on the pixel value of the pathology specimen image that is reproduced by the image reproducer; and wherein the terminal device further comprises a display that displays the observation image.

8. The microscope system according to claim 1, the model property information being a conversion equation that converts the pixel value of the pathology specimen image to the pigment content of the pigment.

9. The microscope system according to claim 1, the pigment property information of the model base profile including the pigment spectral data selected by the spectral data selector.

10. The distribution system according to claim 2, the model property information being a conversion equation that converts the pixel value of the pathology specimen image to the pigment content of the pigment.

11. The distribution system according to claim 2, the pigment property information including the pigment spectral data selected by the spectral data selector.

* * * * *